US008433396B2

(12) United States Patent
Ferek-Petric (10) Patent No.: US 8,433,396 B2
(45) Date of Patent: Apr. 30, 2013

(54) METHODS AND APPARATUS FOR ATRIOVENTRICULAR SEARCH (75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 2012 days.

(21) Appl. No.: 10/418,856

(22) Filed: Apr. 18, 2003

(65) Prior Publication Data
US 2004/0215262 A1 Oct. 28, 2004

(51) Int. Cl.
A61B 5/0205 (2006.01)
(52) U.S. Cl.
USPC ............................................ 600/510; 607/25
(58) Field of Classification Search .................... 607/25; 600/510
See application file for complete search history.

(56) References Cited

U.S. PATENT DOCUMENTS

| 4,966,146 | A | * | 10/1990 | Webb et al. ...................... 607/19 |
| 5,024,222 | A | * | 6/1991 | Thacker ............................ 607/22 |
| 5,042,497 | A | | 8/1991 | Shapland ........................ 128/696 |
| 5,243,976 | A | | 9/1993 | Ferek-Petric et al. |
| 5,261,418 | A | | 11/1993 | Ferek-Petric |
| 5,271,392 | A | | 12/1993 | Ferek-Petric |
| 5,316,001 | A | | 5/1994 | Ferek-Petric et al. |
| 5,318,595 | A | | 6/1994 | Ferek-Petric et al. |
| 5,330,511 | A | * | 7/1994 | Boute .............................. 607/25 |
| 5,419,338 | A | * | 5/1995 | Sarma et al. .................... 600/516 |
| 5,454,838 | A | | 10/1995 | Vallana et al. |
| 5,466,245 | A | * | 11/1995 | Spinelli et al. .................. 607/17 |
| 5,496,351 | A | | 3/1996 | Plicchi et al. |
| 5,507,782 | A | | 4/1996 | Kieval et al. ...................... 607/9 |
| 5,609,612 | A | | 3/1997 | Plicchi et al. |
| 5,626,620 | A | * | 5/1997 | Kieval et al. ...................... 607/9 |
| 5,693,074 | A | | 12/1997 | Ferek-Petric |
| 5,693,075 | A | | 12/1997 | Plicchi et al. |
| 5,713,930 | A | * | 2/1998 | van der Veen et al. .......... 607/25 |
| 5,861,007 | A | | 1/1999 | Hess et al. |
| 6,073,048 | A | * | 6/2000 | Kieval et al. .................... 607/17 |
| 6,161,041 | A | * | 12/2000 | Stoop et al. ..................... 607/14 |
| 6,678,547 | B2 | * | 1/2004 | Carlson et al. ................. 600/515 |
| 2001/0020136 | A1 | | 9/2001 | Sweeney et al. .............. 600/515 |
| 2002/0128563 | A1 | | 9/2002 | Carlson et al. ................ 600/509 |

FOREIGN PATENT DOCUMENTS

WO WO 99/10042 A1 4/1999

OTHER PUBLICATIONS

Kowallik, P. et al., "Independent Autonomic Modulation of the Human Sinus and AV Nodes: Evidence from Beat-to-Beat Measurements of PR and PP Intervals During Sleep," *J Cardiovasc Electrophysiol*, vol. 6, No. 11, p. 993-1003 (Nov. 1995).

Kowallik, P. et al., "Different Vagal Modulation of the Sinoatrial Node and AV Node in Patients with Congestive Heart Failure," *Clin Sci* (Colch), Suppl. 1, p. 58-61 (1996).

(Continued)

*Primary Examiner* — Joseph Stoklosa
(74) *Attorney, Agent, or Firm* — Reed A. Duthler; Stephen W. Bauer (57) ABSTRACT In general, the invention provides for commencing an atrioventricular (AV) search in response to an indicator of an autonomic nervous system (ANS) activity. An implantable medical device (IMD) may be configured to apply this technique, and also to apply rate adaptive ventricular pacing. In response to ANS activity such as an abrupt increase in cardiac sympathetic nervous activity, the IMD performs an AV search to find the intrinsic AV interval of the patient. The invention includes selection of a maximum AV delay so that the AV search will not adversely affect hemodynamic function.

22 Claims, 6 Drawing Sheets

OTHER PUBLICATIONS

Leffler, C.T. et al., "Rate-Related and Autonomic Effects on Atrioventricular Conduction Assessed Through Beat-to-Beat PR Interval and Cycle Length Variability," *J Cardiovas Electroohysiol*, vol. 5, No. 1, p. 2-15 (Jan. 1994).

Victor, J. et al., "Influence of the Autonomic Nervous System on the Normal and Pathological Atrioventricular Node," *Arch Mal Coeur Vaiss*, vol. 80, No. 10, p. 1471-1477 (Sep. 1987).

Warner, M.R. et al., "Beat-by-Beat Modulation of AV Conduction. 1. Heart Rate and Respiratory Influences," *Am J Physiol*, vol. 251, No. 6, pt. 2, p. H1126-33 (Dec. 1986).

Warner, M.R. et al., "Beat-by-Beat Modulation of AV Conduction. 1. Autonomic Neural Mechanisms," *Am J Physiol*, vol. 251, No. 6, pt. 2, p. H1134-42 (Dec. 1986).

* cited by examiner

METHODS AND APPARATUS FOR ATRIOVENTRICULAR SEARCH

TECHNICAL FIELD

The invention relates to implantable medical devices, and more particularly, to cardiac pacemakers that pace one of more chambers of the heart to provide atrioventricular synchrony.

BACKGROUND

Atrioventricular (AV) synchrony, i.e., the timing of atrial and ventricular contractions, is important for good hemodynamic function in a patient. In a normal cardiac cycle, following a period of passive filling of a heart, the atria of the heart contract to squeeze blood into the ventricles of the heart. When atrial contraction is completed, the ventricles contract to eject blood into the body.

Some patients having problems with AV synchrony may have an implantable medical device (IMD), such as a pacemaker, to monitor AV synchrony and to deliver therapy to promote AV synchrony. The IMD senses atrial and ventricular events. In particular, the IMD senses atrial and ventricular activations triggered by the normal intrinsic autorhythmic activity of the heart itself. The IMD may also deliver electrical stimulations or "paces" to activate one or more atria or one or more ventricles, and thereby trigger atrial or ventricular contractions.

In a normal cardiac cycle, there is a time interval between a sensed or paced atrial activation and a ventricular activation. The time interval between a sensed or paced atrial event and an intrinsic ventricular event is called the "intrinsic AV interval," the "spontaneous AV interval" or the "AV conduction time." The term "intrinsic AV interval" will be used herein to refer to this time interval. In some patients, the ventricles may, from time to time, fail to activate following an atrial activation. When the ventricles fail to activate spontaneously, the IMD may deliver a pacing pulse to one or both ventricles to cause the ventricles to activate.

The IMD is programmed with a parameter known as the "AV delay" or "paced AV delay." The parameter is also known as the "AV interval," but the term "AV delay" will be used herein to refer to the programmable parameter and to distinguish it from the intrinsic AV interval. In general, the AV delay is the interval between a paced or sensed atrial event and a scheduled paced ventricular event. Following an atrial event, the IMD waits for the AV delay, and then paces the ventricle, unless an intrinsic ventricular event occurs prior to the expiration of the AV delay. When the IMD senses an intrinsic ventricular event, the IMD inhibits the ventricular pace for that cardiac cycle, and does not deliver the scheduled ventricular pace.

It is often desirable for the AV delay to be longer than the intrinsic AV interval. In other words, it is often desirable that intrinsic ventricular conduction be preserved, giving the ventricles an opportunity to activate of their own accord. When the ventricles fail to activate, the IMD delivers a ventricular pace. The IMD conserves power by pacing when needed, and by inhibiting pacing when the ventricles activate of their own accord.

To promote intrinsic ventricular conduction, an IMD may be programmed with "AV search" capability. AV search capability is the capacity to find the intrinsic AV interval of the heart using an AV search algorithm. In a typical conventional IMD having AV search capability, an AV search is triggered by an intrinsic ventricular activation that precedes a scheduled ventricular pace. In general, the IMD monitors a number of atrioventricular conduction sequences, monitors whether intrinsic ventricular activations are occurring before the scheduled ventricular paces, and also monitors how close in time the ventricular activations are to the scheduled ventricular paces. Using data collected during the monitoring, the IMD shortens or lengthens the AV delay by an "offset," so that the AV delay is longer than the intrinsic AV interval.

The AV delay applied by the IMD may also be "rate adaptive," i.e., the AV delay may automatically lengthen or shorten in response to various conditions. For example, the AV delay may shorten when the patient is engaging in physical activity, and lengthen when the patient is at rest. The amount of shortening or lengthening is called an "offset." A rate adaptive AV delay typically lengthens or shortens without regard to whether the intrinsic AV interval lengthens or shortens in response to the conditions.

In a conventional IMD, rate adaptive operation and AV search capability are exclusive functions. If AV search capability is enabled, then the rate adaptive capability is disabled, and vice versa.

SUMMARY

In general, the invention enhances the responsiveness of AV search capability, by commencing an AV search in response to an indicator of an autonomic nervous system (ANS) activity. The invention further combines AV search capability and rate adaptive capability in a single IMD, to promote the advantages of each capability.

The invention may be applied, for example, in an IMD that paces one or more ventricles of a patient in a rate adaptive mode. In response to ANS activity such as an abrupt increase in cardiac sympathetic nervous activity, the IMD may discontinue pacing in the rate adaptive mode and perform an AV search. In some patients, the ANS activity signals a shortening of the intrinsic AV interval, in which the patient may be able to sustain intrinsic ventricular activations, i.e., ventricular activations without pacing. In such circumstances, the IMD commences an AV search to determine the intrinsic AV interval.

A typical AV search begins with the IMD increasing the AV delay, and monitoring a number of successive conduction sequences. In particular, the IMD monitors whether intrinsic ventricular activations occur before the scheduled ventricular paces, and if so, by how much time. The IMD adjusts the AV delay, shortening or lengthening the AV delay by an offset, so that the AV delay is about as long as or slightly longer than the intrinsic AV interval. The search is typically an iterative process. The invention provides techniques whereby the number of monitored conduction sequences is a function of the ANS activity.

In some circumstances, an AV search may tend to lengthen the AV delay beyond a point that is hemodynamically beneficial. Such lengthening may occur when the patient engages in physical activity, and the heart rate of the patient increases. Excessive lengthening the AV delay as part of an AV search under such conditions may result in a loss of hemodynamic benefit to the patient. Accordingly, the invention provides for a maximum AV delay as a function of intrinsic or paced heart rate, thereby reducing the risk that the AV delay will be increased to a point that hemodynamic benefit will be lost.

In one embodiment, the invention is directed to a method comprising determining an indicator of an ANS activity of a patient and searching for an intrinsic AV interval as a function of the determination. One indicator of an ANS activity is the Q-T interval, i.e., the duration between the Q-wave and T-wave. An abrupt change in the Q-T interval may indicate a change in sympathetic nervous tone. The invention encompasses any other indicator of an ANS activity, however.

In another embodiment, the invention presents a method comprising determining an indicator of an ANS activity of a patient and selecting a number of AV conduction sequences in a search for an intrinsic AV interval as a function of the determination. Typically, the selected number is larger when parasympathetic nervous system activity is dominant, and smaller when sympathetic nervous system activity is dominant.

In a further embodiment, the invention is directed to a method comprising applying pacing therapy to at least one ventricle of a heart and selecting a maximum AV delay as a function of a heart rate. The heart rate may be paced or intrinsic.

In an additional embodiment, the invention is directed to a method comprising operating a pacemaker in a rate adaptive mode that automatically changes an AV delay in response to a condition other than an intrinsic AV interval, determining an indicator of an ANS activity of a patient, and in response to the determination, commencing an AV search to estimate the intrinsic AV interval.

In further embodiments, the invention comprises computer-readable media comprising instructions for causing a programmable processor to carry out these methods. In other embodiments the invention is directed to an implantable medical device that may practice one or more of the methods.

The details of one or more embodiments of the invention are set forth in the accompanying drawings and the description below. Other features and inventive aspects will be apparent from the description and drawings, and from the claims.

DETAILED DESCRIPTION

Figure 1:
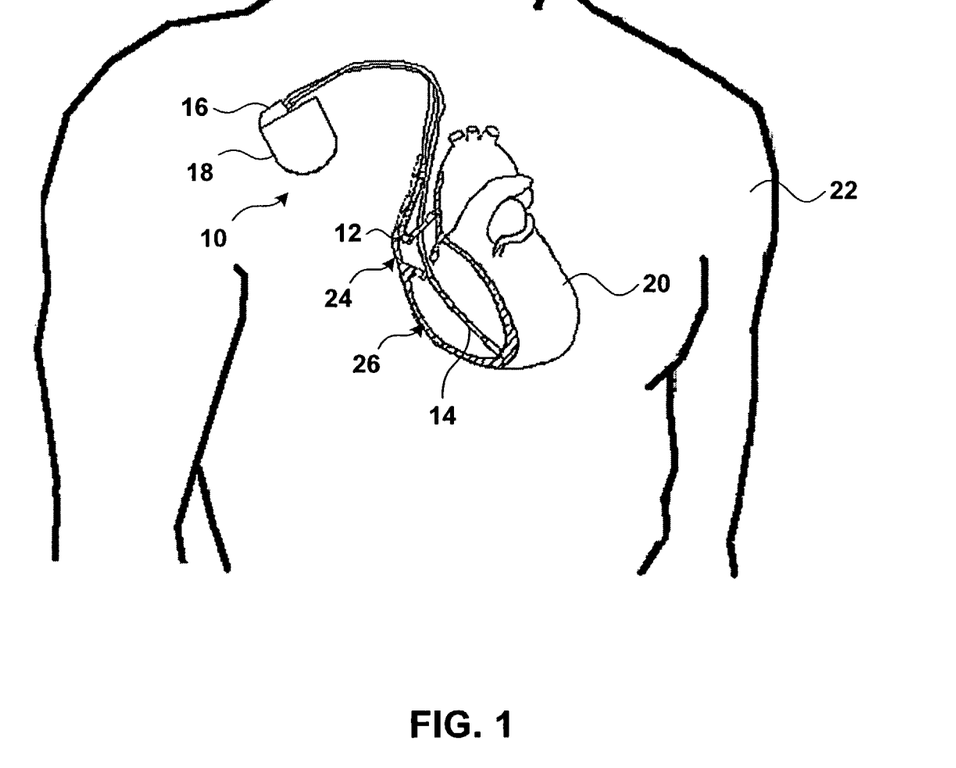
FIG. 1 is a schematic view of an exemplary implantable medical device that may practice the invention.

FIG. 1 is a schematic view of one embodiment of a device that may practice the invention. Implantable medical device ("IMD") 10 is a pacemaker comprising atrial pacing and sensing lead 12 and ventricular pacing and sensing lead 14 attached to connector module 16 of hermetically sealed enclosure 18 and implanted near human or mammalian heart 20 of a patient 22. Pacing and sensing leads 12 and 14 sense electrical signals attendant to the depolarization and repolarization of the heart 20, and further provide pacing pulses for causing depolarization of cardiac tissue in the vicinity of the distal ends thereof. Leads 12 and 14 may have unipolar or bipolar electrodes disposed thereon.

IMD 10 is one example of a device that has the capability practicing the invention, in that IMD 10 has the capability of sensing or pacing at least one atrium, and pacing at least one ventricle. In particular, atrial pacing and sensing lead 12 senses activation of the right atrium 24, and can pace right atrium 24. Ventricular pacing and sensing lead 14 senses activation of the right ventricle 26, and can pace right ventricle 26. IMD 10 is not the only implantable medical device that may practice the invention, however. The invention may be practiced by implantable medical devices that are configured to pace three or four chambers of heart 20, and that provide atrioventricular synchrony.

Figure 2:
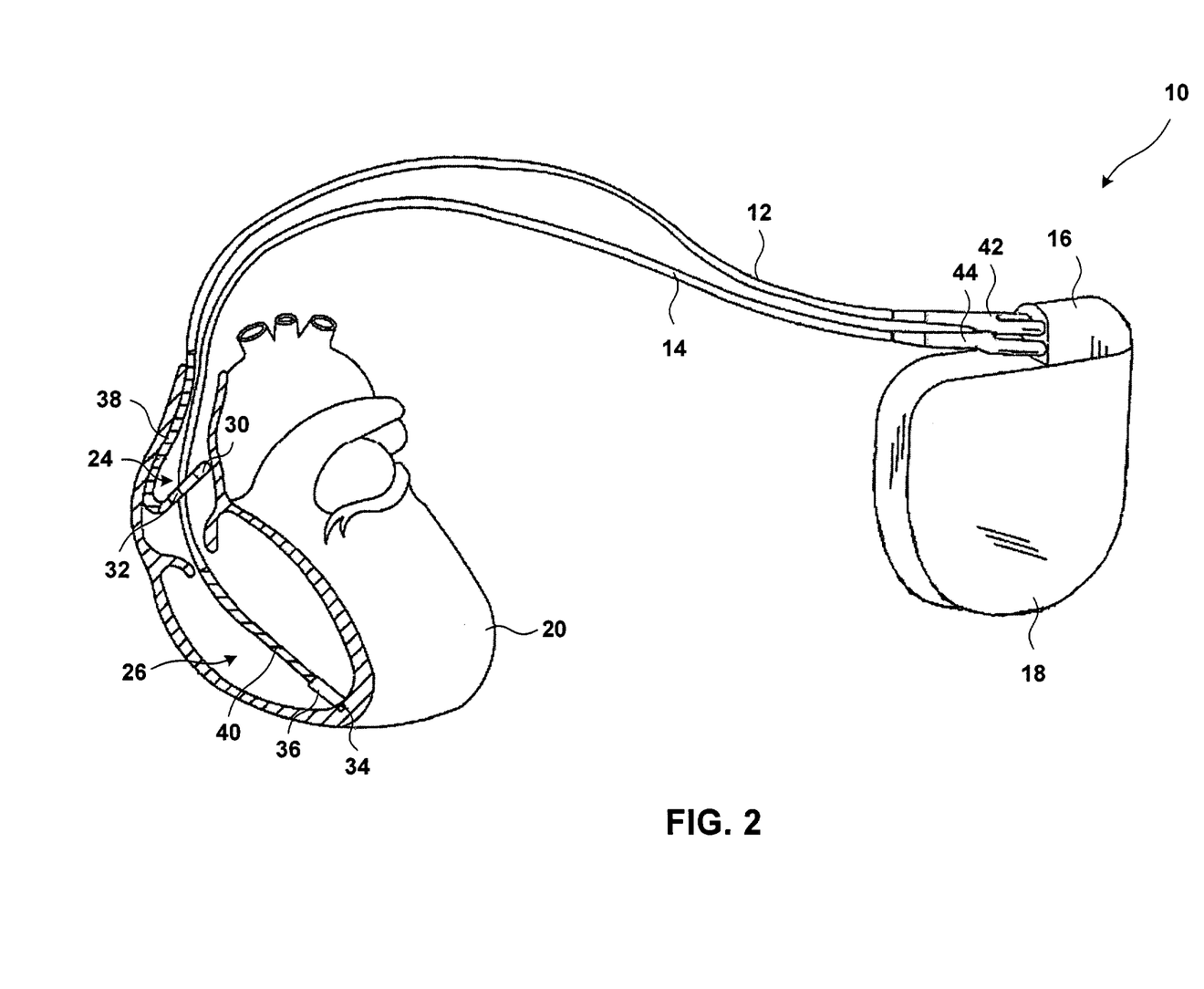
FIG. 2 shows the implantable medical device located in and near a heart.

FIG. 2 shows IMD 10, with connector module 16 and hermetically sealed enclosure 18 located in and near human or mammalian heart 20. Atrial and ventricular pacing leads 12 and 14 extend from connector module 16 to the right atrium 24 and right ventricle 26, respectively, of heart 20. Atrial electrodes 30 and 32 disposed at the distal end of atrial pacing lead 12 are located in right atrium 24. Ventricular electrodes 34 and 36 disposed at the distal end of ventricular pacing lead 14 are located in right ventricle 26. Pulse generators (not shown in FIG. 2) inside enclosure 18 generate pacing pulses. The pacing pulses are delivered to right atrium 24 or right ventricle 26 by electrodes 30, 32, 34, 36.

A processor (not shown in FIG. 2) in IMD 10 directs delivery of paces to promote AV synchrony and good hemodynamic function. In the example IMD 10 shown in FIGS. 1 and 2, the processor applies an AV delay that is ordinarily longer than the intrinsic AV interval, to preserve the intrinsic ventricular conduction of heart 20. The processor directs delivery of a ventricular pace when the ventricles fail to activate prior to the scheduled ventricular pace. The processor may operate in a rate adaptive mode, in which IMD 10 automatically changes the AV delay in response to a physiological condition, such as patient physical activity. The processor may also operate in a "search AV delay" mode, in which IMD automatically changes the AV delay as a function of the intrinsic atrioventricular interval.

In addition to pacing, IMD 10 may apply other forms of therapy, which need not be related to AV synchrony. In FIG. 2, for example, atrial lead 12 and ventricular lead 14 include defibrillation electrodes 38 and 40, respectively. Defibrillation electrodes 38 and 40 deliver defibrillation shocks to right atrium 24 or right ventricle 26.

Atrial and ventricular leads 12,14 each include an elongated insulative lead body carrying one or more conductors insulatively separated from one another. At the proximal end of leads 12,14 are bifurcated connectors 42, 44, which electrically couple the connectors to connector module 16 of IMD 10.

Figure 3:
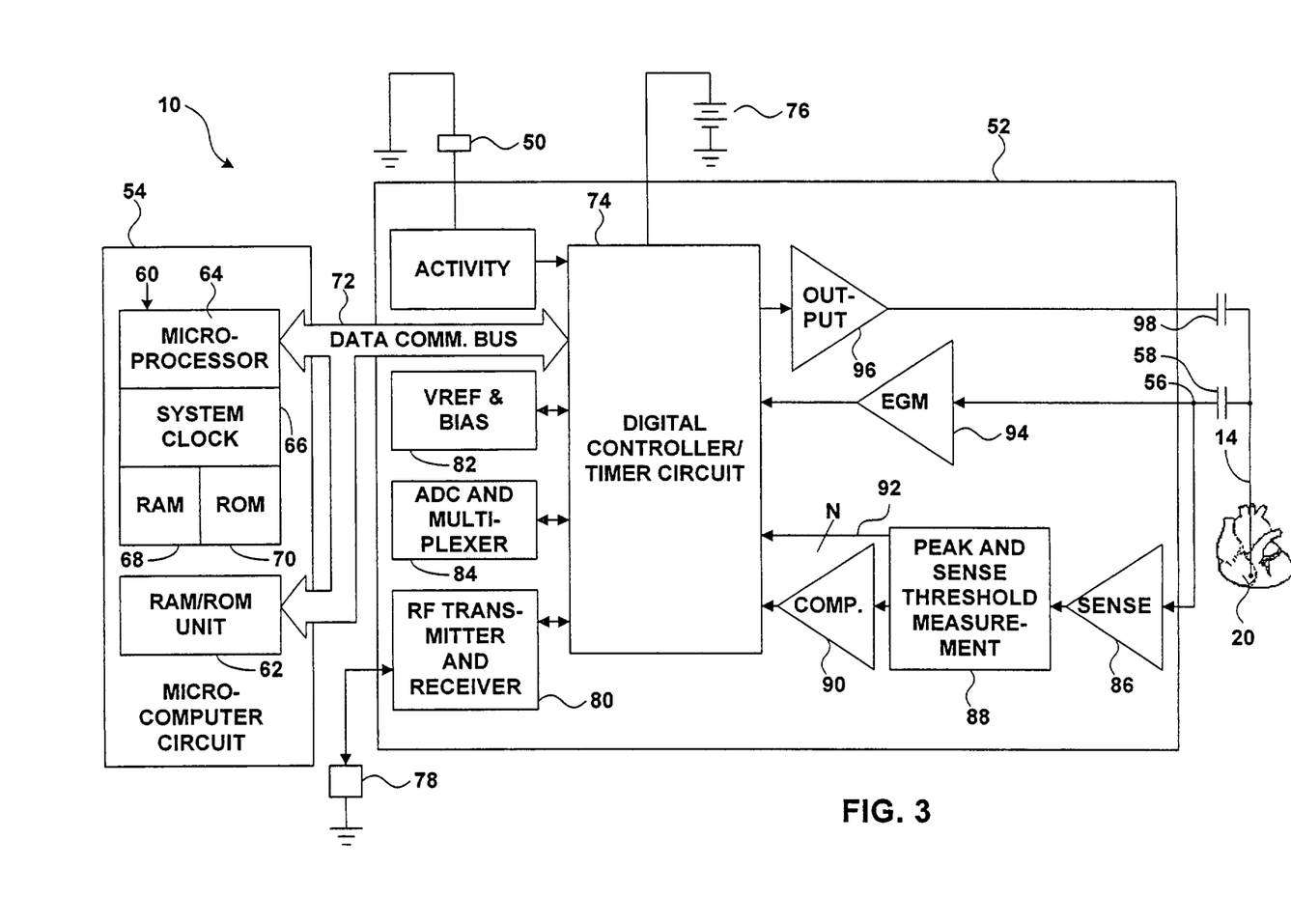
FIG. 3 is a block diagram illustrating the constituent components of the implantable medical device depicted in FIGS. 1 and 2.

FIG. 3 shows a block diagram illustrating the constituent components of IMD 10 in accordance with one embodiment of the invention, in which IMD 10 is a pacemaker having a microprocessor-based architecture. IMD 10 includes one or more activity sensors 50. Activity sensor 50 may include an accelerometer, such as a piezoceramic accelerometer or a microelectromechanical accelerometer, that typically provides a sensor output that varies as a function of a measured parameter relating to a patient's metabolic requirements. In other words, activity sensor 50 detects motion of patient 22 that accompanies physical activity, and may adjust the pacing rate to the metabolic needs associated with the physical activity.

The output of activity sensor 50 is coupled to input/output circuit 52. Input/output circuit 52 contains analog circuits for interfacing with heart 20, activity sensor 50, and other components and circuits for the application of stimulating pulses to heart 20. The rate of heart 20 is controlled by software-implemented algorithms stored within microcomputer circuit 54.

For the sake of convenience, IMD 10 in FIG. 3 is shown with only lead 14 connected. Similar circuitry and connections not explicitly shown in FIG. 3 apply to lead 12 (shown in FIGS. 1 and 2), however. Lead 14 is coupled to node 56 in IMD 10 through input capacitor 58.

Microcomputer circuit 54 comprises on-board circuit 60 and off-board circuit 62. On-board circuit 60 preferably includes microprocessor 64, system clock circuit 66 and on-board random access memory (RAM) 68 and read-only memory (ROM) 70. Off-board circuit 62 comprises a RAM/ROM unit. On-board circuit 60 and off-board circuit 62 are each coupled by data communication bus 72 to digital controller/timer circuit 74. Microcomputer circuit 54 may comprise a custom integrated circuit device augmented by standard RAM/ROM components.

Microcomputer circuit 54 is an example of a processor that directs delivery of paces to promote AV synchrony and good hemodynamic function, and may do so in concert with digital controller/timer circuit 74. Microcomputer circuit 54 is further an example of a processor that controls the duration of an AV delay, and that determines whether IMD 10 operates in a rate adaptive mode or a search AV delay mode.

Electrical components shown in FIG. 3 are powered by an appropriate implantable battery power source 76. For the sake of clarity, the coupling of battery power to the various components of IMD 10 is not shown in FIG. 3.

Antenna 78 is connected to input/output circuit 52 to permit uplink/downlink telemetry through radio frequency (RF) transmitter and receiver telemetry unit 80. IMD 10 in FIG. 3 is programmable by an external programming unit (not shown in the figures) that communicates with IMD 10 via antenna 78 and RF transmitter and receiver telemetry unit 80.

VREF and Bias circuit 82 generates stable voltage reference and bias currents for analog circuits included in input/output circuit 52. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 52.

Digital controller/timer circuit 74 is coupled to sensing circuitry, including sense amplifier 86, peak sense and threshold measurement unit 88 and comparator/threshold detector 90. Sense amplifier 86 amplifies electrical cardiac signals sensed via lead 14 and provides an amplified signal to peak sense and threshold measurement circuitry 88, which in turn provides an indication of peak sensed voltages and measured sense amplifier threshold voltages on multiple conductor signal path 92 to digital controller/timer circuit 74. An amplified sense amplifier signal is also provided to comparator/threshold detector 90.

Digital controller/timer circuit 74 is further coupled to electrogram (EGM) amplifier 94 for receiving amplified and processed signals sensed by lead 14. The electrogram signal provided by EGM amplifier 94 is employed, for example, when IMD 10 is being interrogated by an external programmer to transmit a representation of a cardiac analog electrogram. Output pulse generator 96 provides amplified pacing stimuli to heart 20 through coupling capacitor 98 in response to a pacing trigger signal provided by digital controller/timer circuit 74.

IMD 10 may sense the R-R interval, i.e., the interval between ventricular activations, via sense amplifier 86, peak sense and threshold measurement unit 88 and comparator/threshold detector 90. The R-R interval is directly related to the rate at which heart 20 beats. Consequently, sense amplifier 86, peak sense and threshold measurement unit 88 and comparator/threshold detector 90 may serve as a heart rate sensor or a heart interval sensor. The heart rate, alone or in concert with another physiological signal, may be used as an indicator of autonomic nervous system (ANS) activity. The heart rate may further be used as a parameter for changing the AV delay, as will be described below.

IMD 10 may sense other intervals as well, such as the Q-T interval. In some embodiments of the invention, the Q-T interval may be sensed via analysis of the electrogram signal from EGM amplifier 94. In other embodiments of the invention, IMD 10 may sense the Q-T interval by a sensor not shown in FIG. 3. As will be described below, the Q-T interval is a physiological signal that includes an indicator of ANS activity.

IMD 10 may further include one or more other sensors (not shown) to sense other physiological signals that include an indicator of ANS activity. Alternatively, IMD 10 may receive signals from one or more other sensors that sense other physiological signals.

One example of such a sensor is a pressure sensor that responds to a blood pressure such as arterial blood pressure. Blood pressure is another physiological signal that, alone or in concert with another physiological signal, includes an indicator of ANS activity. The pressure sensor may be disposed in a chamber of heart 20, e.g., on the distal end of lead 14, or may be deployed at another site in or around the cardiovascular system. IMD 10 may receive pressure signals from the pressure sensor, and may process the signals, e.g., by taking a derivative to observe changes in blood pressure over time.

As will be discussed below, other sensors that sense physiological signals that include an indicator of ANS activity include a myocardial contractility sensor and a blood flow sensor. The invention encompasses any physiological signal that includes an indicator of an ANS activity, sensed via any sensor. IMD 10 may process signals generated as a function of any physiological effect to determine an indicator of ANS activity.

Figure 4:
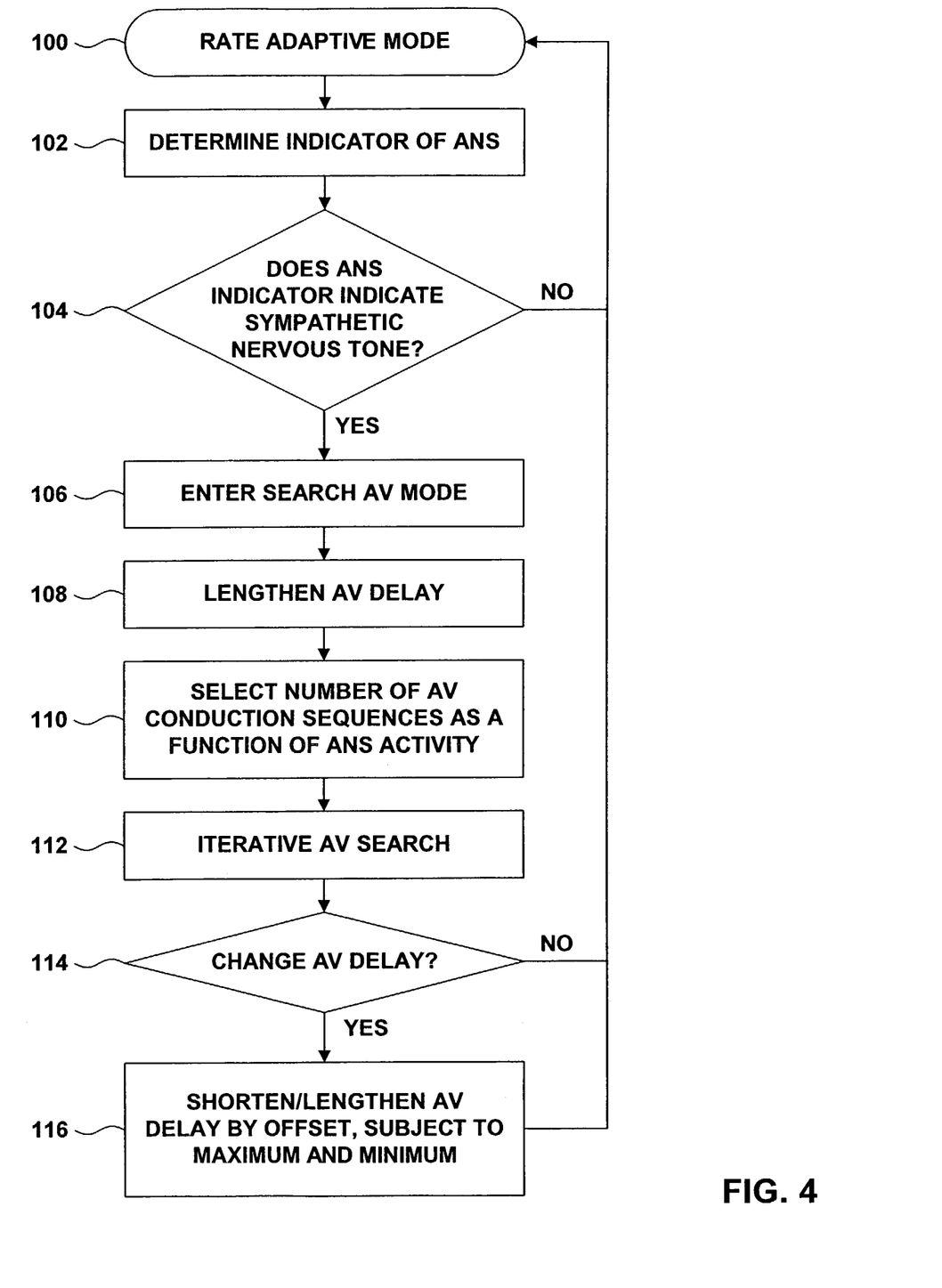
FIG. 4 is a flow diagram illustrating techniques of the invention that may be performed by an implantable medical device, such as the implantable medical device depicted in FIGS. 1-3.

FIG. 4 is a flow diagram illustrating techniques that may be performed by IMD 10 in accordance with one or more embodiments of the invention. For purposes of illustration, it is assumed that IMD 10 operates in rate adaptive mode (100). In rate adaptive mode, IMD 10 may lengthen or shorten the AV delay in response to a condition. For example, IMD 10 may adjust the AV delay in response to activity sensed by activity sensor 50. The invention is not limited to an IMD that operates in rate adaptive mode, however, but may be applied by an IMD that applies a fixed AV delay as well.

IMD 10 determines an indicator of ANS activity (102). The indicator reflects ANS activity, and IMD 10 monitors ANS activity by monitoring the indicator. IMD 10 may, for example, monitor ANS activity intermittently, or may monitor ANS activity continuously. When the indicator indicates sympathetic nervous tone (104), IMD 10 enters a search AV mode to find the intrinsic AV interval (106). An indicator may indicate sympathetic nervous tone when, for example, sympathetic stimulation of the heart is dominant over parasympathetic stimulation by a predefined degree, or when there is an abrupt increase in sympathetic stimulation.

The invention encompasses any indicator of ANS activity. One example of an indicator of ANS activity is the Q-T interval. An abrupt shortening of the Q-T interval may indicate an increase in sympathetic nervous activity, particularly cardiac sympathetic nervous activity. This technique will be described in more detail in connection with FIG. 5.

Another indicator of ANS activity may be the sympathovagal balance, as reflected in one or more physiological signals. IMD 10 may, for example, receive physiological signals that include one or more indicators of sympathetic nervous activity or parasympathetic nervous activity. Such physiological signals may include, for example, heart rate and blood pressure. The signals may be processed to separate sympathetic and parasympathetic components, and the magnitude of the sympathetic component may be compared to the magnitude of the parasympathetic component to determine whether sympathetic activity is dominant, and by what degree.

Another indicator of ANS activity is cardiac contraction, which is measurable by several techniques. Sympathetic stimulation increases the cardiac contraction force, and thus increases the velocity of blood flow. Accordingly, a measure of blood flow such as tricuspid blood flow, measurable by a blood flow sensor, is a further possible indicator of ANS activity. In general, parasympathetic stimulation causes opposite effects, i.e., decreased contraction force and decreased blood flow velocity. Any or all of these indicators of ANS activity may be employed. When one or more indicators indicate sympathetic nervous tone (104), IMD 10 triggers an AV search (106).

An AV search typically involves monitoring and examination of a number of conduction sequences, such as sixteen conduction sequences. Each conduction sequence represents a sensed or paced atrial activation, followed by a sensed or paced ventricular activation.

A typical AV search is an iterative process. IMD 10 begins with a starting AV delay, which schedules ventricular paces at a certain time after a sensed or paced atrial event. IMD 10 monitors whether intrinsic ventricular activations are occurring before the scheduled ventricular paces, and if so, by how much time. IMD 10 then determines whether to adjust the AV delay, i.e., whether to shorten the AV delay, whether to lengthen the AV delay, or whether to keep the AV delay the same. When the AV delay is kept the same, then IMD 10 has finished its search, and has found the AV delay that promotes intrinsic ventricular conduction but also supplies ventricular paces when needed.

The AV delay may be lengthened when a percentage of conduction sequences end in paces. If, for example, fifteen of the sixteen most recent conduction sequences ended with a ventricular pace, then the AV delay is probably shorter than the intrinsic AV interval. Accordingly, IMD 10 may prolong the AV delay by the amount of one offset. A typical offset may be, for example, 31 milliseconds. As will be described below in connection with FIG. 6, the amount of the offset need not be constant.

The AV delay may also be lengthened when a percentage of conduction sequences end with ventricular activations that precede the scheduled ventricular paces by a very brief time margin. If, for example, four of the sixteen most recent conduction sequences ended with a ventricular pace, and ten of the sequences ended with an intrinsic ventricular activation that is less than 15 milliseconds before the scheduled ventricular pace, then the AV delay is about as long as or slightly longer than the intrinsic AV interval. Accordingly, IMD 10 may lengthen the AV delay by the amount of one offset, to improve the chances of intrinsic ventricular activation.

The AV delay may be shortened when a percentage of conduction sequences end with ventricular activations that precede the scheduled ventricular paces by a large time margin. If, for example, fifteen of the sixteen most recent conduction sequences ended with an intrinsic ventricular activation that is 55 milliseconds or more before the scheduled ventricular pace, then AV delay may be substantially longer than the intrinsic AV interval. Accordingly, IMD 10 may shorten the AV delay by the amount of one offset so that the AV delay will more closely follow the intrinsic AV interval.

When a percentage of conduction sequences end with ventricular activations that neither very early nor very late, then IMD 10 has concluded its AV search, and the AV delay remains unchanged. IMD 10 may be programmed to apply any criteria for determining whether ventricular activations are very early or very late, and may be programmed to determine how many early or late conduction sequences may be tolerated with causing an adjustment to the AV delay.

An AV search may begin with an automatic increase in the AV delay by one offset (108). This lengthening of the AV delay improves the chance of intrinsic ventricular activation, thereby improving the chances of finding the intrinsic AV interval. This lengthened AV delay becomes the starting AV delay for the AV search.

The AV search may further entail IMD 10 selecting a number of conduction sequences for monitoring and examination (110). As noted above, the number of conduction sequences may be a fixed number, such as sixteen conduction sequences. The invention provides, however, that the selected number of conduction sequences need not be a fixed number. Rather, the number of conduction sequences is selected as a function of ANS activity. In general, the number of conduction sequences is small when the degree of sympathetic activity is high, and the number of conduction sequences is large when the degree of sympathetic activity is low. When the patient experiences a high degree of sympathetic activity, for example, the AV search may be performed with four conduction sequences. When the patient experiences a low degree of sympathetic activity, on the other hand, the AV search may be performed with more conduction sequences. In this way, IMD 10 is more promptly responsive to ANS activity and associated changes in the intrinsic AV interval.

After selection of a number of conduction sequences (110), an iterative AV search begins (112), as described above. When an adjustment to the AV delay is in order (114), an the AV delay may be increased or decreased by the amount of the offset (116). A typical IMD may be programmed with maximum and minimum AV delays, so that the AV delay may not be increased or decreased indefinitely. As will be described below in connection with FIG. 6, the maximum AV delay may be rate-adaptive. The selected offset may be a constant or variable.

In the event no adjustment to the AV delay is in order (114), IMD 10 may remain in AV search mode or may return to rate adaptive mode (100). Whether IMD 10 returns to rate adaptive mode may be a function of ANS activity. Whether IMD 10 returns to rate adaptive mode may also be a function of whether IMD 10 has adjusted the AV delay by the maximum allowable. In that event, the AV search has failed to find the intrinsic AV interval, or ventricular pacing according to the AV delay would be more hemodynamically beneficial to the patient than intrinsic ventricular activation according to the intrinsic AV interval.

Figure 5:
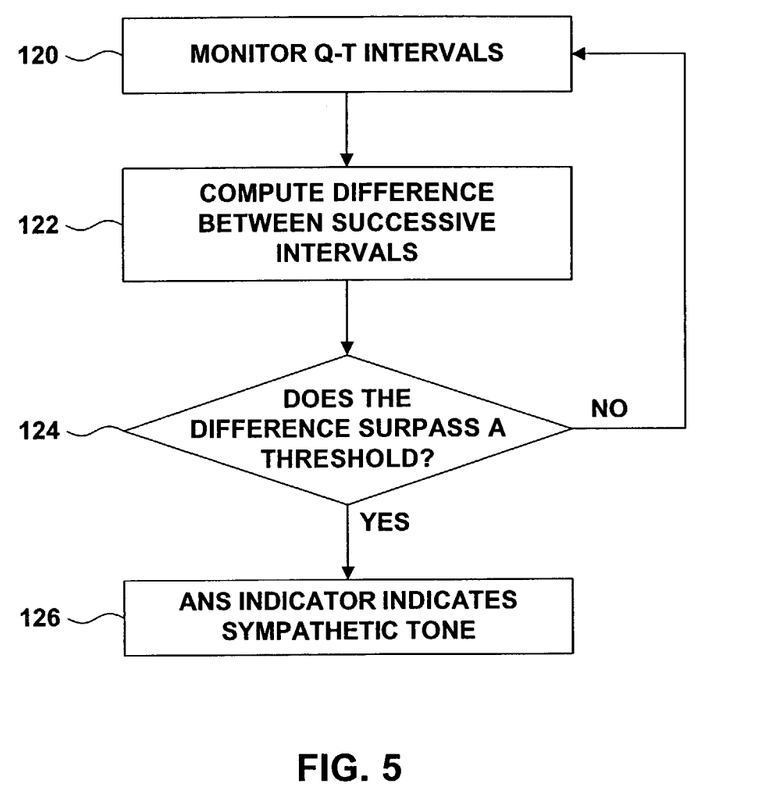
FIG. 5 is a flow diagram illustrating a technique for determining an indicator of autonomic nervous system activity as a function of changes in Q-T intervals.

FIG. 5 is a flow diagram illustrating a technique for determining an indicator of ANS activity. IMD 10 monitors Q-T intervals (120), which reflect the ANS activity. In particular, autonomic tone influences the duration of the Q-T interval, with sympathetic activity causing the interval to shorten.

In general, a change in ANS activity would be reflected in a change in the duration of the Q-T interval. Accordingly, IMD 10 computes the difference between successive Q-T intervals (122), to determine whether 0-T intervals are demonstrating an abrupt change. When the difference surpasses a threshold (124), then IMD 10 determines that the Q-T indicator indicates sympathetic tone (126). IMD 10 may trigger an AV search to find the intrinsic AV interval, as shown in FIG. 4.

An abrupt change in Q-T intervals may also be reflected by plotting the Q-T intervals and taking the first derivative of the plot. When the first derivative surpasses a threshold, IMD 10 determines that the Q-T indicator indicates sympathetic tone.

Figure 6:
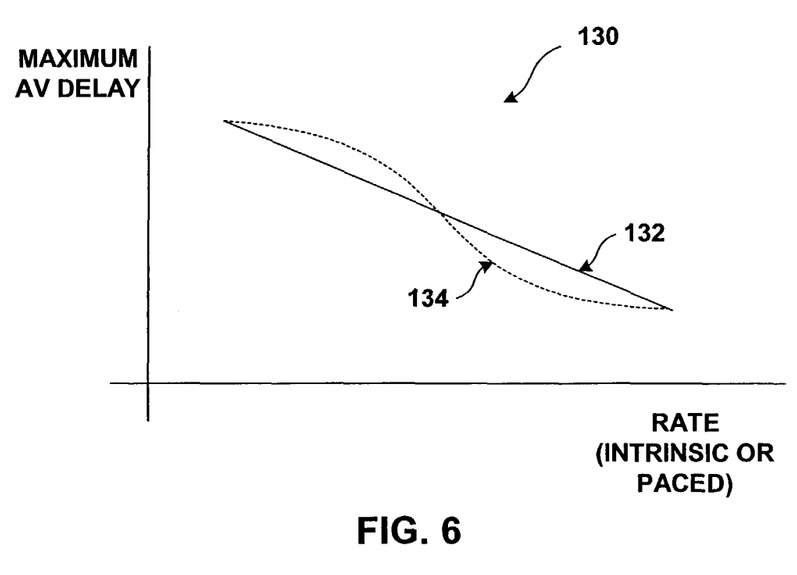
FIG. 6 is a graph illustrating a relation between a selected maximum atrioventricular delay and a heart rate, in accordance with an embodiment of the invention.

FIG. 6 is a graph 130 illustrating selection of a variable maximum AV delay as a function of intrinsic or paced heart rate. During an AV search, the AV delay may be iteratively increased as IMD 10 searches for the intrinsic AV interval. In some circumstances, however, continual increases of the AV interval are not hemodynamically beneficial to the patient. At some point, IMD 10 must pace deliver a ventricular pace, whether the intrinsic AV interval is found or not, and must discontinue lengthening the AV delay. When the heart rate of the patient is high, lengthening the AV delay should be discontinued more quickly than when the heart rate is low.

When the patient begins physical activity, for example, and the patient's intrinsic or paced heart rate increases to meet the metabolic needs associated with the physical activity, ventricular activations generally need to follow shortly after atrial activations. Excessive lengthening the AV delay as part of an AV search may result in a loss of hemodynamic benefit to the patient. When the patient engages in prolonged physical activity, continued lengthening of the AV delay may have serious consequences. In an extreme illustrative case, ventricular and subsequent atrial diastolic filling waves may overlap, resulting in "pacemaker syndrome" and a dramatic reduction of cardiac output.

When the patient is relatively at rest, by contrast, and has a low heart rate, there is less adverse hemodynamic in lengthening the AV delay as a part of an AV search. Accordingly, the maximum AV delay when the patient has a high heart rate is less than when the patient has a low heart rate. The relation between heart rate and maximum AV delay may be a straight line 132, or a curve 134.

The effect of having a maximum AV delay as a function of heart rate, as shown in FIG. 6, is a combination of AV search capability and rate-adaptive capability. An AV search may be performed at any heart rate, but the AV search will be subject to a variable maximum AV delay, reducing the risk that the AV search will adversely affect the hemodynamics of the heart. In effect, the reduced maximum AV delay at high heart rates effectively causes IMD 10 to discontinue the search for the intrinsic AV interval and resume rate-adaptive pacing.

The invention combines the benefits of AV search capability and rate-adaptive capability in other ways as well. A sudden increase in sympathetic activity can precede a shortening of the intrinsic AV interval, and in such circumstances, it may be beneficial to preserve intrinsic ventricular conduction. By triggering an AV search with sympathetic activity, an IMD may predict that intrinsic ventricular conduction may be about to occur and may promptly begin an AV search to promote intrinsic ventricular conduction. Moreover, the search is adaptive to find the intrinsic AV interval quickly. When the degree of sympathetic activity is high, the selected number of AV conduction sequences may be low, to facilitate a faster search.

Many embodiments of the invention have been described. Various modifications may be made without departing from the scope of the claims. For example, the invention is not limited to the particular implantable medical devices described above, but may be practiced by a wide variety of implantable medical devices.

In addition, the invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

These and other embodiments are within the scope of the following claims.

The invention claimed is:

1. A method comprising:
   sensing a physiological condition of a patient used as an indicator of autonomic nervous system activity;
   determining a presence and measurement of autonomic nervous system activity of a patient based upon the sensed physiological condition indicator of such activity;
   selecting a set of search criteria based upon the measurement of the autonomic nervous system activity; and
   invoking a search with the selected search criteria for an atrioventricular (AV) delay upon a determination of the presence of autonomic nervous system activity of a patient, to promote intrinsic ventricular conduction and supply ventricular paces when needed, wherein the search further includes monitoring intrinsic ventricular activations to determine a time of occurrence before scheduled ventricular paces and adjusting an applied AV delay based upon the monitored intrinsic ventricular activations.

2. The method of claim 1, wherein determining the presence of the autonomic nervous system activity is based upon a sensing of sympathetic nervous tone.

3. The method of claim 1, wherein determining the presence of the autonomic nervous system activity is based upon a sensing of a change in a Q-T interval.

4. The method of claim 3, further comprising:
   measuring a change in two successive Q-T intervals; and
   searching for the intrinsic atrioventricular interval when the change surpasses a predetermined threshold.

5. The method of claim 1, wherein determining the presence of the autonomic nervous system activity comprises determining a sympatho-vagal balance.

6. The method of claim 1, wherein determining the presence of the autonomic nervous system activity comprises determining at least one of cardiac sympathetic nervous activity and cardiac parasympathetic nervous activity.

7. The method of claim 1, wherein determining the presence of the autonomic nervous system activity comprises:
   detecting at least one physiological signal that includes a sympathetic activity indicator and a parasympathetic activity indicator;
   determining the sympathetic activity indicator;
   determining the parasympathetic activity indicator; and
   estimating the relative magnitude of the sympathetic activity indicator in comparison to the parasympathetic activity indicator.

8. The method of claim 1, wherein sensing a physiological condition of a patient comprises sensing at least one of cardiac contractility, blood flow and blood pressure.

9. The method of claim 3, further comprising increasing a paced atrioventricular delay in response to the change.

10. The method of claim 1, wherein searching for the atrioventricular interval comprises selecting a number of conduction sequences.

11. The method of claim 10, wherein searching for the atrioventricular interval delay further comprises:
monitoring the percentage of the number of conduction sequences in which an intrinsic ventricular activation occurs before a scheduled ventricular pace; and
monitoring the percentage of the number of conduction sequences in which a ventricular pace occurs.

12. The method of claim 1, wherein searching for the atrioventricular interval delay comprises increasing a paced atrioventricular delay by an offset.

13. The method of claim 1, wherein searching for the atrioventricular interval delay comprises decreasing a paced atrioventricular delay by an offset.

14. A method comprising:
sensing a physiological condition of a patient used as an indicator of autonomic nervous system activity;
determining autonomic nervous system activity of a patient based upon the sensed physiological condition indicator of such activity; and
selecting a number of atrioventricular (AV) conduction sequences in a search for an AV delay that promotes intrinsic ventricular conduction and that supplies ventricular paces when needed, the search being invoked in response to a determination of the presence of autonomic nervous system activity of a patient, wherein the search includes monitoring intrinsic ventricular activations to determine a time of occurrence before scheduled ventricular paces and includes adjusting an applied AV delay; further comprising:
selecting a first number of atrioventricular conduction sequences;
selecting a second number of atrioventricular conduction sequences when the determination indicates an increase in sympathetic nervous system activity relative to parasympathetic nervous system activity, wherein the second number is smaller than the first number.

15. An implantable medical device comprising:
a sensor to sense an indicator of autonomic nervous system activity of a patient;
an implantable pulse generator to generate pacing pulses;
at least one electrode coupled to the implantable pulse generator to deliver the pacing pulses to a ventricle of the patient; and
a processor to determine autonomic nervous system activity based at least in part upon the sensed indicator and to search for an atrioventricular (AV) delay that promotes intrinsic ventricular conduction and supplies ventricular paces when needed by monitoring intrinsic ventricular activations to determine a time of occurrence before scheduled ventricular paces and adjusting an applied AV delay, wherein the processor searches for the atrioventricular delay if autonomic nervous system activity is determined and the processor selects and applies a set of search criteria based upon the determined activity.

16. The device of claim 15, wherein the electrode is further configured to sense activation of the ventricle.

17. The device of claim 15, wherein the electrode comprises the sensor.

18. The device of claim 15, wherein the electrode is a first electrode, the device further comprising a second electrode coupled to the implantable pulse generator to deliver the pacing pulses to an atrium of the patient.

19. The device of claim 15, wherein the processor is configured to detect a change in a Q-T interval and to determine the indicator of autonomic nervous system activity as a function of the change.

20. The device of claim 15, wherein the processor is configured to process signals generated as a function of at least one of cardiac contractility, blood flow and blood pressure.

21. The device of claim 15, wherein the processor is further configured to increase a paced atrioventricular delay.

22. The device of claim 15, wherein the processor is further configured to select a number of conduction sequences as a function of the determination.

* * * * *